(12) United States Patent
Munafo' et al.

(10) Patent No.: US 9,610,315 B2
(45) Date of Patent: Apr. 4, 2017

(54) COMPOSITIONS FOR THE TREATMENT OF GASTRO-ESOPHAGEAL REFLUX DISEASE (GERD)

(75) Inventors: Salvatore Munafo', Santa Venerina (IT); Luisa Rizza, Santa Venerina (IT)

(73) Assignee: BIONAP S.R.L., Santa Venerina (IT)

(*) Notice: Subject to any disclaimer, the term of this patent is extended or adjusted under 35 U.S.C. 154(b) by 213 days.

(21) Appl. No.: 13/144,413

(22) PCT Filed: Jan. 15, 2010

(86) PCT No.: PCT/EP2010/000211
§ 371 (c)(1),
(2), (4) Date: Sep. 14, 2011

(87) PCT Pub. No.: WO2010/081720
PCT Pub. Date: Jul. 22, 2010

(65) Prior Publication Data
US 2011/0318432 A1  Dec. 29, 2011

(30) Foreign Application Priority Data
Jan. 16, 2009  (EP) .................................... 09425009

(51) Int. Cl.
| | | |
|---|---|---|
| *A61K 9/00* | (2006.01) |
| *A01N 43/16* | (2006.01) |
| *A61K 36/00* | (2006.01) |
| *A61K 9/02* | (2006.01) |
| *A61K 9/48* | (2006.01) |
| *A61K 36/63* | (2006.01) |
| *A61K 47/10* | (2006.01) |
| *A61K 36/33* | (2006.01) |
| *A61K 36/60* | (2006.01) |

(52) U.S. Cl.
CPC .................................... *A61K 36/60* (2013.01)

(58) Field of Classification Search
CPC .......... A61K 36/33; A61K 9/02; A61K 47/10; A61K 36/63; A61K 9/4858; A61K 9/0031; A61K 2300/00
See application file for complete search history.

(56) References Cited

U.S. PATENT DOCUMENTS

2007/0014876 A1*  1/2007  Shapira et al. ............... 424/682
2007/0203242 A1*  8/2007  Calton ......................... 514/565

FOREIGN PATENT DOCUMENTS

| WO | 02/060391 A2 | 8/2002 |
|----|--------------|--------|
| WO | 2009/060024 A1 | 5/2009 |

OTHER PUBLICATIONS

Annex IX Classification Criteria (1993L0042-EN-11.10.2007-005. 001, p. 52-56).*
Galati E. M. et al.: "Opuntia ficus indica (L.) Mill. mucilages show Cytoprotective Effect on Gastric Mucosa in Rat", Phytotherapy Research, John Wiley & Sons Ltd. Chichester, GB, vol. 21, No. 4, Apr. 1, 2007, pp. 344-346, XP002476118, ISSN: 0951-418X, Cited in ISR.
Bretagne J. et al.: "Gastroesophageal reflux disease (GERD) in the French Population: Results of an observational Survey performed in a sample of nearly 8000 subjects of 18 years of age and above", Gastroenterology, Elsevier, Philadelphia, PA, vol. 126, No. 4, Suppl. 2, Apr. 1, 2004, p. A311, XP009125950, ISSN: 0016-5085, Cited in ISR.
Wade W. et al.: "Gastroesophageal reflux disease in the elderly" Journal of Geriatric Drug Therapy, Haworth Press, Binghamton, US, vol. 12, No. 1, Jan. 1, 1997, pp. 3-14, XP009125945, ISSN: 8756-4629, Cited in ISR.
Chavez D. et al.: "The Nopal: A Plant of Manifold Qualities", World Review of Nutrition and Dietetics, Karger, Muenchen, DE, vol. 77, Jan. 1, 1995, p. 109-134, XP001053507, ISSN: 0084-2230, p. 125, line 10-line 12, p. 126, line 34-line 37, Cited in ISR.
International Search Report, dated Jul. 20, 2010, from corresponding PCT application.

* cited by examiner

*Primary Examiner* — Sue Liu
*Assistant Examiner* — Helen Chui
(74) *Attorney, Agent, or Firm* — Young & Thompson (57) ABSTRACT

Oral pharmaceutical, nutraceutical, health foods and medical device compositions based on polysaccharides from *Opuntia Ficus Indica* cladodes in combination with other active substances are useful for the prevention or treatment of GERD (Gastro-Esophageal Reflux Disease), gastric esophagitis and related diseases (e.g. dyspepsia, esophagitis, esofageal tumour, gastro-intestinal symptoms, chronic pharyngitis, Barrett's esophagus, esophageal adenocarcinoma, GERD-related pulmonary symptoms).

4 Claims, 6 Drawing Sheets

| Sample | Mucoadhesion percentage value (% ± DS) |
|---|---|
| Sodium Alginate 0.5% | 5.36 ± 0.24 |
| Opuntia Ficus Indica cladodes polysaccharides 0.5% | 55.81 ± 2.34* |
| Sodium Alginate 0.5% + Opuntia Ficus Indica cladodes polysaccharides 0.5% | 74.83 ± 3.10** |

Fig. 4

| Treatment and dose | Ulceration index (percent inhibition) | |
|---|---|---|
| | Ethanol | Indomethacin |
| F (control) | 5.80±0.22 | 5.11±0.26 |
| A (alginate/bicarbonate) | 4.65±0.18* (19.31) | 4.13±0.26* (19.17) |
| B (*O. ficus indica* polysaccharides) | 5.14±0.24* (11.37) | 4.32±0.18* (15.48) |
| C (*O. europea* leaves extract) | 5.25±0.28* (9.48) | 4.35±0.22* (14.87) |
| D (alginate/bicarbonate/*O. ficus indica* polysaccharides) | 3.70±0.29** (36.20) | 3.41±0.15** (33.26) |
| E (alginate/bicarbonate/*O. ficus indica* polysaccharides/*O. europea* leaves extract) | 2.03±0.36** § (65.00) | 1.42±0.18** § (72.21) |

\* $P < 0.05$ versus control, \*\* $P < 0.01$ versus control

§ $P < 0.05$ versus D (alginate/bicarbonate/*O. ficus indica* polysaccharides)

Fig. 5

| Treatment | Ulceration index (percent inhibition) |
|---|---|
| | Pyloric ligation |
| F (control) | 4.68±0.25 |
| A (alginate/bicarbonate) | 3.72±0.33 * (20.51) |
| B (*O. ficus indica* polysaccharides) | 4.05±0.36 * (13.46) |
| C (*O. europea* leaves extract) | 3.84±0.29 * (17.94) |
| D (alginate/bicarbonato/*O. ficus indica* polysaccharides) | 3.07±0.31 ** (34.40) |
| E (alginate/bicarbonato/*O. ficus indica* polysaccharides/*O. europea* leaves extract) | 1.65±0.24 ** § (64.95) |

* $P < 0.05$ versus control, ** $P < 0.01$ versus control

§ $P < 0.05$ versus D (alginate/bicarbonate/*O. ficus indica* polysaccharides)

Fig. 6

COMPOSITIONS FOR THE TREATMENT OF GASTRO-ESOPHAGEAL REFLUX DISEASE (GERD)

The present invention provides oral pharmaceutical, nutraceutical, health foods and medical device compositions based on polysaccharides from *Opuntia Ficus Indica* cladodes, for the prevention or treatment of GERD (Gastro-Esophageal Reflux Disease), gastric esophagitis and related diseases, including dyspepsia, esophagitis, esofageal tumour, gastro-intestinal symptoms, chronic pharyngitis, Barrett's esophagus, esophageal adenocarcinoma, GERD-related pulmonary symptoms, preferably in combination with different active substances for the same medical indications. These compositions, which proved to act synergistically, enables to use a lower effective dose of actives, improving their therapeutic index.

BACKGROUND OF THE INVENTION

Esophageal reflux occurs in physiological conditions, in particular in newborns, but when it overcomes the esofageal mucosa defence mechanisms, it may cause diseases such as GERD.

GERD is the more frequent gastric disease and it is due to gastric or enteric reflux in the esophagus, leading to reflux esophagitis, a very common disease with typical esophageal mucosa inflammation and lesions (erosions and small ulcers) due to the gastric or enteric juice reflux in the esophagus.

In GERD the reflux lead to symptoms similar to esophagitis, but not to lesions.

Normally a pressure gradient between esophagus and stomach inhibits the back flow of gastric contents in the esophagus.

The anatomical structure mainly involved in maintaining the pressure gradient is the LES (Lower Esophageal Sphincter), a muscular ring at the esophagus and stomach joint, which relaxes during swallowing.

In physiological conditions, when gastric (acid) substances reflux in the esophagus, the esophageal peristalsis (esophageal muscle contractions) push them back to the stomach, and their acid residues are buffered and neutralized by the saliva swallowed.

GERD is characterized by similarity between pressures in the esophagus and in the stomach, respectively. This could be due to:
lowered or absent LES tone;
LES relaxation in the absence of swallowing;
Reduced elimination of acidic material caused by abnormal esophageal peristalsis;
Abnormal function of cardias, the valve between stomach and esophagus that inhibits, in physiological conditions, the reflux of gastric contents in the esophagus.

The imperfect cardias closure may be due to different causes, such as obesity, smoke, multiple pregnancies, hard physical efforts, pharmacological treatments or hiatus hernia.

The serious types of reflux esophagitis may lead to esophagus stricture (stenosis) caused by esophagitis healing at the recovery, or to precancerous lesions ("Barrett's esophagus", esofageal adenocarcinoma) that produce an esophageal mucosa metaplasia, taking typical appearance of gastric or duodenal mucosa. In some patients other factors are involved such as lowered saliva secretion, exaggerated acidic secretion, delayed gastric emptying, biliary salts or pancreatic enzymes reflux.

These diseases are characterized by heartburn (hard retrosternal burning), burps and food or acid regurgitation in the mouth. These symptoms can be associated with others affecting the respiratory system (chronic cough, asthma, hoarseness, chronic laryngitis) teeth (enamel losing) or ear (otalgia).

GERD and reflux esophagitis, in case of acidic reflux, are currently treated with 1) proton pump inhibitors (PPI, e.g. omeprazole, lansoprazole) $H_2$ receptor antagonists (e.g. cimetidine and ranitidine), that reduce the acidic gastric secretion and consequently the reflux; 2) prokinetic agents (e.g. metoclopramide, domperidone, laevosulpiride), that increase the cardias valve tone and improve the gastric emptying; 3) antacid agents (e.g. bicarbonate, magnesium and aluminium hydroxide) and cytoprotective agents (e.g. sucralfate), that reduce gastric acidity and protect esophageal mucosa.

Only few drugs are useful in case of non-acid (enteric) regurgitation.

Dietary, postural and behavioural rules that help to reduce or to prevent symptoms are associated with the pharmacological therapy. For example, it is recommended to avoid alcohol, abundant meals or fatty, spicy or irritant foods (mint, chocolate, coffee, tea), and to sleep with a pillow raised by some centimetres.

The pharmacological therapy does not affect the disease's cause (ill-functioning cardias) and it must be taken for very long periods (even the entire life) as almost all patients suffer from disease recurrence once the therapy is interrupted.

The dysfunctional cardias valve closure may be corrected with surgical therapy: this leads to perfect recovery from the disease, but if it is not well performed it may determine the appearance of new symptoms. Moreover, the surgical treatment is recommended for young subjects, in excellent general condition and who are in need of continuous high dose therapy. Recently Dr. Higa proposed a new surgical method able to reduce GERD, but this new technique is not very widespread.

There are not clear indications for preferring one specific pharmacological therapy for the treatment of GERD or reflux esophagitis: physicians choose in general on the basis of their personal experience. Consequently, the choice of the therapy is very personal and not objective and it is possible that a physician has to try more than one pharmacological therapy prior to find the therapy best fitting the patient's physiology.

For patients with mild or occasional symptoms antacid agents, prokinetic agents, alginates and, in the most serious cases, $H_2$ antagonists (anti $H_2$) and proton pump inhibitors (PPI) are recommended.

Step up clinical protocols—where less effective drugs are gradually joined to or replaced by more effective actives, on the basis of symptomatology—and step down clinical protocols—where the therapy begins with highly effective actives such as proton pump inhibitors and continues with less effective actives—are provided for (Bytzer P., *Goals of therapy and guidelines for treatment success in symptomatic gastroesophageal reflux disease patients*, Am. J. Gastroenterol. 2003; 98(3) Suppl: S31-S39).

PPIs are much effective actives, but their prolonged use (which is needed in reflux esophagitis therapy) revealed serious side effects related to the long-term therapy with this class of actives such as increased risk of hip fracture as a result of calcium erratic absorption due to induction of hypochlorhidya (Yang et al., *Long term proton pomp inhibitor therapy and risk of hip fracture*, JAMA 2006, 296(94): 2947-2953), muscle diseases as well as polymyositis and rabdomiolisis (Clark et al., *Myopathy including polymyositis: a likely class adverse effect of proton pump inhibitors?*, Eur. J. Clin. Pharmacol., 2006 June, 62(6): 473-479).

Various PPI's side effects were reported from drug control data generated in Spain from the 1 Jan. to the 31 Dec. 2004 by Salquiero et al. (Salquiero et al., *Safety profile of proton pump inhibitors according to the spontaneous reports of suspected adverse reactions*, Int. J. Clin. Pharmacol. Ther., 2006 November, 44 (11): 548-556).

Alginates, which have a physical mechanism of action (gelling and foaming at the acidic gastric pH, in presence of $HCO_3^-$) are safer than PPIs, but are not useful in the treatment of non-acid esophageal reflux (Zentlin et al., *An evaluation of the antireflux properties of sodium alginate by means of combined multichannel intraluminal impedance and pH-metry*, Aliment Pharmacol Ther. 2005; 21: 29-34).

On the basis of the aforesaid and of the fabt that diseases such as GERD, reflux esophagitis and related diseases (dyspepsia, esophagitis, esophageal tumour, gastrointestinal disorders, chronic pharyngitis, Barrett's esophagus, esofageal adenocarcinoma, GERD-related pulmonary dysfunctions) are increasing, it is highly desirable to find a safe and effective treatment for the prevention and therapy of such diseases, avoiding the patient to undergo different treatments at the same time to obtain an effective therapeutic result.

DESCRIPTION OF THE INVENTION

The invention provides pharmaceutical, nutraceutical, health foods and medical device compositions able to co-operate in a synergistic way with active substances useful in the prevention and therapy of acid and non-acid esophageal reflux diseases and their clinical complications. These compositions are characterized by containing a polysaccharide extract from *Opuntia Ficus Indica* cladodes.

*Opuntia Ficus Indica* (Nopal) is a plant belonging to Cactaceae, native to Mexico and to United States southwest, but widespread even in self-sown Mediterranean vegetation.

Fruits and younger cladodes (more tender) are used from ancient times for dietary use (the cladodes are used fresh, brined, pickled, candied, as jam and even as forage) or to prepare alcoholic drinks.

In popular medicine the plant is used in many ways: fruits are astringent and were used by sailors to prevent scorbutus, thanks to their vitamin C content; young cladodes are used as cataplasm (oven warmed) and as emollient agents; the use of cladodes pulp on cutaneous wounds and ulcers is an excellent anti inflammatory, reepithelialising and healing remedy. It represents an old Sicilian traditional remedy used still nowadays in the country tradition; the flowers decoction has diuretic properties.

More recently it was observed that: 1) *Opuntia Ficus Indica* fruits have marked antioxidant properties (Tesoriere et al., *Supplementation with cactus pear (Opuntia ficus-indica) fruit decreases oxidative stress in healthy humans: a comparative study with vitamin C*, Am J Clin Nutr. 2004 August; 80(2): 391-395); 2) an *Opuntia Ficus Indica* extract is effective in the alcohol hangover therapy (Wiese J et al., *Effect of Opuntia Ficus Indica on symptoms of the alcohol hangover*, Arch Intern Med. 2004 Jun. 28; 164(12): 1334-1340); 3) the high polysaccharide concentration of *Opuntia* cladodes, essentially formed by a polymer of galactose, arabinose and other sugars, has the property of linking swallowed fat and sugars (so preventing their absorption) thereby improving glyco-lipidic metabolisms and metabolic syndrome; 4) *Opuntia Ficus Indica* cladodes mucilages and pectins proved to be gastro protective in experimental animal models (Vazquez-Ramirez R. et al., *Reversing gastric mucosal alterations during ethanol-induced chronic gastritis in rats by oral administration of Opuntia Ficus Indica mucilage*, World J. Gastroenterol. 2006 Jul. 21; 12(27): 4318-4324). Trombetta et al. (Trombetta D. and al., *Effects of polysaccharides from Opuntia Ficus Indica (L.) cladodes on the healing of dermal wounds in the rat*, Phytomedicine, 13 (2006) 352-358) observed that polysaccharides extracted from *Opuntia Ficus Indica* cladodes have cutaneous healing effect on cellular matrix.

It has now unexpectedly found that polysaccharides extracted from *Opuntia Ficus Indica* cladodes exert synergistic activities with substances useful for the prevention and treatment of GERD and its complications.

Accordingly, the invention provides pharmaceutical, nutraceutical, health foods and medical device formulations suitable for oral administration, comprising polysaccharides extracted from *Opuntia Ficus Indica* cladodes, preferably in combination with active substances used for the prevention and therapy of diseases of the upper gastrointestinal tract and particularly GERD, reflux esophagitis and related diseases (dyspepsia, esophagitis, esophageal tumour, gastrointestinal disturbs, chronic pharyngitis, Barrett's esophagus, esophageal adenocarcinoma, pulmonary dysfunctions GERD related). The active substances used in combination with the polysaccharides extracted from *Opuntia Ficus Indica* cladodes include, but are not limited to, antacid agents, proton pump inhibitors, $H_2$ antagonists, prokinetic agents, sodium bicarbonate, alginic acid or alginates, chitosanes, aluminum hydroxide, calcium or magnesium carbonate, antioxidant and anti-inflammatory flavonoides extracted from plants as well as from olive leaves or Capparis Spinosa buttons, anthocianosides from red oranges, black rice or from other natural sources, and their combinations.

These compositions allow to reduce the dose of pharmacologically active substances and possess high therapeutic safety, which is particularly important in children, pregnant women and elderly people, or in those cases where long therapy with NAIDS (Non Steroidal Anti Inflammatory Drugs) is co-administered.

This allows to carry out an effective and safe topically targeted treatment, capable to prevent or cure gastrointestinal tract diseases such as dyspepsia, esophagitis, esophageal tumour, Barrett's esophagus, esophageal adenocarcinoma, GERD-related pulmonary dysfunctions, also in combination with other therapies for the same diseases.

A first aspect of the invention is therefore the provision of pharmaceutical, nutraceutical, health foods and medical device oral compositions comprising polysaccharides from *Opuntia Ficus Indica* cladodes preferably in combination with active substances useful to prevent or cure upper gastrointestinal tract diseases, as defined in the attached claims.

According to the present invention, the term "combination" indicates either a physical or a functional association of extracts and active substances. In the first case (physical association) the active ingredients are formulated in the same composition with carriers, excipients or other ingredients suitable for the purpose of use. In the latter case (functional association) the active ingredients can be administered in separate compositions or through separate routes, in order to reach a combined therapeutic effect.

A second aspect of the invention is the use of said compositions for the preparation of a medicament to treat GERD, dyspepsia, esophagitis, esophageal tumour, gastrointestinal disturbs, chronic pharyngitis, Barrett's esophagus, esophageal adenocarcinoma, pulmonary dysphunctions GERD related, in combination with active substances known to prevent and cure the same diseases, whose efficacy is increased by the synergistic activity of *Opuntia Ficus Indica* cladodes polysaccharides, such active substances being preferably selected from antacid agents, proton pump inhibitors, H2 antagonists, prokinetic agents, sodium bicarbonate, alginic acid or alginates, chitosanes, aluminium or magnesium hydroxide, calcium or magnesium carbonate, antioxidant and anti-inflammatory flavonoides extracted from plants as well as from olive leaves or Capparis Spinosa buttons, anthocianosides from red oranges, black rise or from other natural sources and their combinations.

According to the present invention, *Opuntia Ficus Indica* cladodes polysaccharides—which are optionally supported by maltodextrins (up to 50%)—can be provided in the form of mucilages, which can be isolated through cladode squeezing or by treatment with water at ambient temperature. Alternatively, the cladodes are pressed, the thus obtained juice is centrifuged and the liquid supernatant is subjected to ultrafiltration, thereby obtaining an aqueous solution enriched in polysaccharides (Molecular Weight higher than $10^4$ Da). Subsequently the aqueous solution can be concentrated and dried. The polysaccharide content in the *Opuntia ficus indica* cladode extract generally ranges from 1 to 70% by weight. The chemical structure and composition of *Opuntia ficus indica* cladode polysaccharide has been studied and characterized (D. McGarvie, H. Parolis, Methylation analysis of the mucilage of *Opuntia ficus indic*. Carbohydrate Research, (1981) 88: 305-314; M. S. Karawya et al. Mucilages and Pectines of *Opuntia*, Tamarindus and *Cydonia*. Planta Medica (1980) Supplement:68-75; M. E. Malainine et al. Structure and morphology of cladodes and spines of *Opuntia ficus indica*. Cellulose extraction and characterisation. Carbohydrate polymers (2003) 51:77-83).

The mucilages are made of residues of 1,4-α-D-galactopyranosyl-uronic acid and 1,2-β-L-rhamnopyranosides which are attached to short 1,6-β-D-galactopyranose chains in position 4 of all rhamnopyranose residues. Most of galctoside residues bear chains in O-3 or O-4 which mainly consist of arabinofuranoside, arabinofuranoside-xylopyranoside residues (D. McGarvie, H. Parolis, Methylation analysis of the mucilage of *Opuntia ficus indic*. Carbohydrate Research, (1981) 88: 305-314). The mucilages contained in *Opuntia ficus indica* cladodes are generally isolated through a squeezing process (D. Trombetta et al. Effect of polysaccharides from *Opuntia ficus-indica* (L.) cladodes on the healing of dermal wounds in the rat. *Phytomedicine* (2006) 13: 352-358) or by water treatment (R. Vázquez-Ramírez et al. Reversing gastric mucosal alterations during ethanol-induced chronic gastritis in rats by oral administration of *Opuntia ficus-indica* mucilage. *World J Gastroenterol* (2006) 12(27):4318-4324).

The compositions of the invention can be liquid or solid, suitable for oral administration, preferably in the form of oral solutions, oral suspensions, oral emulsions, tablets, powders and tablets for extemporaneous preparation. As used herein, the term "medical device" means an "Active medical device" (class I) in accordance with the Directive 93/42/EEC Annex IX classification.

The compositions of the invention may include preservatives, ionic and non ionic buffered agents and additives commonly used in the preparation of oral compositions.

For liquid oral compositions such as solutions, suspensions or emulsions, the solvent is preferably water or a multiple-component aqueous solution compatible with the oral use.

The active substances useful for treating or preventing upper gastrointestinal tract diseases to be used in combination with the *Opuntia Ficus Indica* cladodes extract of the invention include: 1) substances yet used for the cure of the same diseases such as proton pump inhibitors, H2 antagonists, prokinetic agents, antacid agents, sodium bicarbonate, alginic acid or alginates, chitosanes, sodium bicarbonate and their combinations; 2) natural substances such as antioxidant and anti inflammatory flavonoides from plants, e.g. from Capparis Spinosa buttons, antocyanosides from red oranges, black rice or other natural sources and preferably extracts of olive leaves; 3) combinations between 1) and 2).

*Olea europeae* leaves can be extracted with aqueous or hydroalcoholic solvents (10-80% ethanol) at ambient temperature or heating up to 60-70° C., or by treatment with microwaves, ultrasounds or by superheated liquid extraction (Lee O. H. et al. Assessment of phenolics-enriched extract and fractions of olive leaves and their antioxidant activities Bioresour Technol (2009) *Epub ahead of print*; Mylonaki S. et al. Optimisation of the extraction of olive (*olea europaea*) leaf phenolics using water\ethanol-based solvent systems and response surface methodology. *Anal Bioanal Chem.* (2008) 392(5):977-85; Japón-Lujan R, Luque de Castro M D. Small branches of olive tree: a source of biophenols complementary to olive leaves. *J Agric Food Chem.* (2007) 30; 55(11):4584-8; Vassiliki T Papoti, Maria Z. Tsimidou. Impact of sampling parameters on the radical scavening potential of olive (*Olea europeae* L.) leaves. *J Agric Food Chem* 2009, 57, 3470-3477; Japón-Luján R, Luque de Castro M D. Superheated liquid extraction of oleuropein and related biophenols from olive leaves. *J Chromatogr A.* (2006) 1136(2):185-91). The hydroalcoholic extraction process can be repeated several times to obtain an enrichment in biophenols. Once the extraction is terminated, the aqueous or hydroalcoholic solvent is removed under vacuum at 40° C. Further enrichment in biophenols can be obtained by loading the dried extract onto styrene resins and eluting with 50:50 ethanol/water solution.

The *Olea europeae* leaves extract contains phenols (tyrosol, hydroxytyrosol and derivatives thereof), cinnamic acids, flavonoids (apigenin, luteolin and glucoside derivatives thereof, rutin, quercetin), lignans, secoiridoids (oleuroside, oleuropeine and derivatives thereof, elenolic acid) and specifically contains the following polyphenolic profile: 2-40% flavonoids (apigenin, luteolin and derivatives thereof), 0.5-10% oleuropeine, 1-30% hydroxytyrosol and derivatives thereof.

Methods for preparing pharmaceutical or nutraceutical compositions are known in the art. The content of *Opuntia Ficus Indica* extracted polysaccharides preferably ranges from 0.5 to 50% w/w of the total compositions; the other actives may be in amounts from 1 to 30%.

The *Opuntia ficus indica* polysaccharides, which are currently used in dietaries, are suitable and safe for particular patients categories such as elderly people, children or pregnant women.

The present invention further provides the use of the compositions for treating and preventing upper gastrointestinal tract diseases by administration of therapeutically effective amounts of *Opuntia* polysaccharides to a subject in need thereof, preferably in combination with active substances useful for treating or preventing the same diseases.

The pathological conditions that may benefit from treatment with the compositions of the present invention include: gastroesophageal reflux, GERD, dyspepsia, esophagitis, and esophageal tumour, gastrointestinal disturbs, chronic pharyngitis, Barrett's esophagus, esophageal adenocarcinoma, GERD-related pulmonary dysfunctions.

BRIEF DESCRIPTION OF THE FIGURES

Further characteristics and advantages of the present invention will be more evident from the following description and non-limiting examples with reference to the attached figures, wherein.

Non limiting examples of compositions according to the invention are reported in the following tables.

TABLE 1

Oral suspension 1

| Components | % |
|---|---|
| Polysaccharides from *Opuntia Ficus Indica* cladodes | 2 g |
| Water | up to 100 ml |

TABLE 2

Oral suspension 2

| Components | % |
|---|---|
| Sodium Alginate | 5 g |
| Sodium Bicarbonate | 2.67 g |
| Polysaccharides from *Opuntia Ficus Indica* cladodes | 2.0 g |
| Water | up to 100 ml |

TABLE 3

Oral powder (bags) 1

| Components | Amount |
|---|---|
| Sodium Alginate | 10-20 g |
| Sodium Bicarbonate | 5-10 g |
| Polysaccharides from *Opuntia Ficus Indica* cladodes | 1-20 g |

TABLE 4

Oral powder (bags) 2

| Components | Amount |
|---|---|
| Sodium Alginate | 10-20 g |
| Sodium Bicarbonate | 5-10 g |
| Olive leaves extract | 5-20 |
| Polysaccharides from *Opuntia Ficus Indica* cladodes | 1-20 g |

TABLE 5

Capsule 1

| Components | mg/capsule |
|---|---|
| Cimetidine | 200 mg |
| Polysaccharides from *Opuntia Ficus Indica* cladodes | 100-200 mg |
| Olive leaves extract | 100-200 mg |
| Lactose | up to capsule filling |

TABLE 6

Capsule 2

| Components | mg/capsula |
|---|---|
| Ranitidine chloridrate | 84 mg |
| Alginic acid | 500.0 mg |
| Polysaccharides from *Opuntia Ficus Indica* cladodes | 200 mg |
| Olive leaves extract | 200 mg |
| Sodium bicarbonate | 165.25 mg |
| Magnesium stearate | 0.75 mg |
| Filler | 350 mg |

In Vitro Determination of Mucoadhesion of Polysaccharides from *Opuntia Ficus Indica* Cladodes Alone and in Combination with Alginic Acid on Buccal Mucosae Epithelial Cells In order to assess the mucoadhesive capability of polysaccharides from *Opuntia Ficus Indica* cladodes, the in vitro mucoadhesion assay described by Patel (Patel D. and al., *An in vitro mucosal model predictive of bioadhesive agents in the oral cavity*. J Control Release, 1999, 61(1-2): 175-183) was applied to suspended epithelial cells from buccal mucosa. In this test, mucoadhesion (adhesive capability of the tested substances to the mucosal cells) is determined as a function of lectin-membrane glycoprotein binding inhibition induced by the cellular surface-masking due to the mucoadhesive substance.

Materials and Methods

The treatment of mucosal cells with biotinylated lectin and streptavidin peroxidase confer a yellow colour to the sample; pre-treatment of mucosal cells with a mucoadhesive substance (30° C., for 15 minutes before the treatment with lectin) hides the lectin binding site, reducing the final yellow colouring intensity.

Lectin is a protein contained in some plants of Leguminosae (*Canavalia ensiformis*), with high tendency to bind glucosidic and mannosidic residues of membrane glycoproteins; biotin (vitamin H) is bonded to lectin through streptavidin peroxidase that is added to cellular suspension to obtain the complex protein-glucose-lectin-biotin-streptavidin peroxidase.

Figure 1:
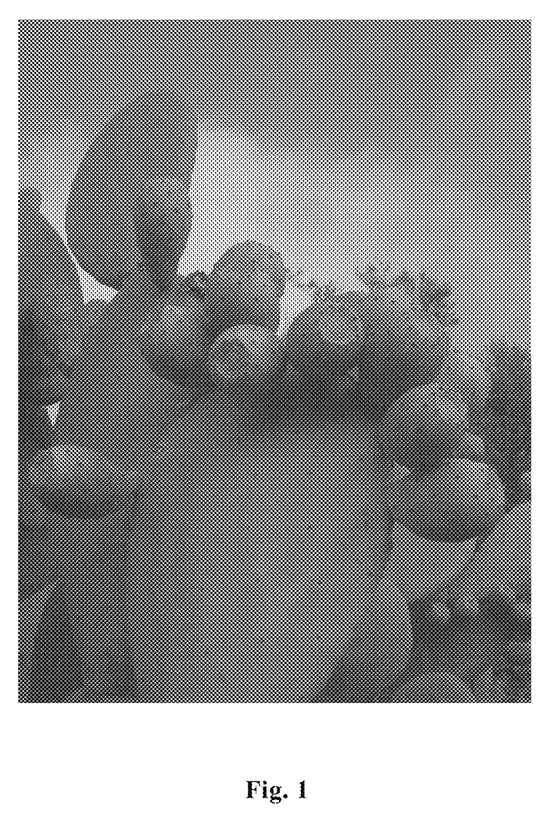
FIG. 1: photograph of cladodes and fruits of *Opuntia Ficus Indica*.
Figure 2:
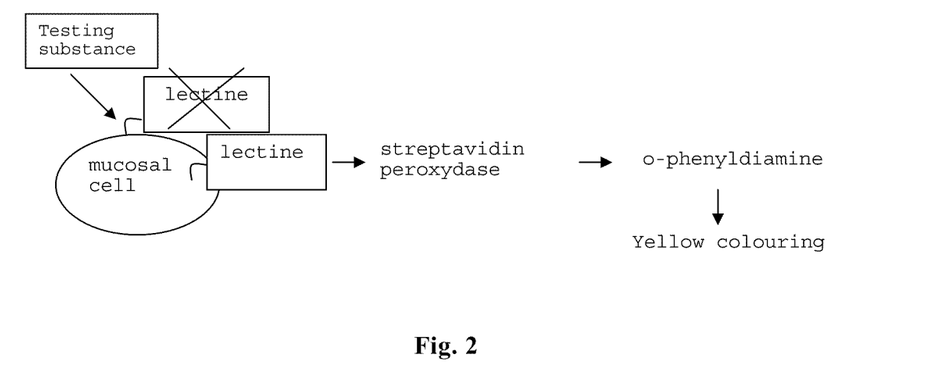
FIG. 2: in vitro model of mucoadhesion.

By addition of o-phenylendiamine dihydrochloride (o-pd) and hydrogen peroxide to the cellular suspension, o-pd is oxidized by the complex protein-glucose-lectin-biotin-streptavidin peroxidase to 2,3-diaminophenazine, and the sample becomes yellow (FIG. 2).

The reaction is then blocked after 1 min adding $H_2SO_4$ 1M. The colour intensity is read at the spectrofluorimeter and it is proportionally related to the binding between lectin and glycosidic residues on cellular membrane.

Buccal mucosa cells were obtained from male and female healthy volunteers, by gently scraping the inner cheek with a wooden spatula. The cells were then pulled and suspended in 10 ml isotonic Tris 0.05M (TBS) pH 7.6 (Patel D. et al., *An in vitro mucosal model predictive of bio-adhesive agents in the oral cavity*. J Control Release, 1999, 61(1-2): 175-183). A suspension sample was then added (0.1 ml trypan blue 0.5% (w/v)) and the total number of cells was determined using an haemocytometer: each sample contained $48 \times 10^4$ buccal mucosa cells. Polysaccharides from *Opuntia Ficus Indica* cladodes and sodium alginate were solubilised in NaCl 0.9% isotonic solution at 0.5% w\v and these solutions were then used for the pre-treatment of buccal mucosa cells. Results are expressed as percentage of tested substance and mucosa cells binding, which is inversely proportional to percent reduction of sample colouring compared to the control.

The whole experiment was repeated 5 times for the control and for each tested substance.

Statistical analysis of results was performed by means of one-way ANOVA followed by Bonferroni post hoc test.

Results

Figure 3:
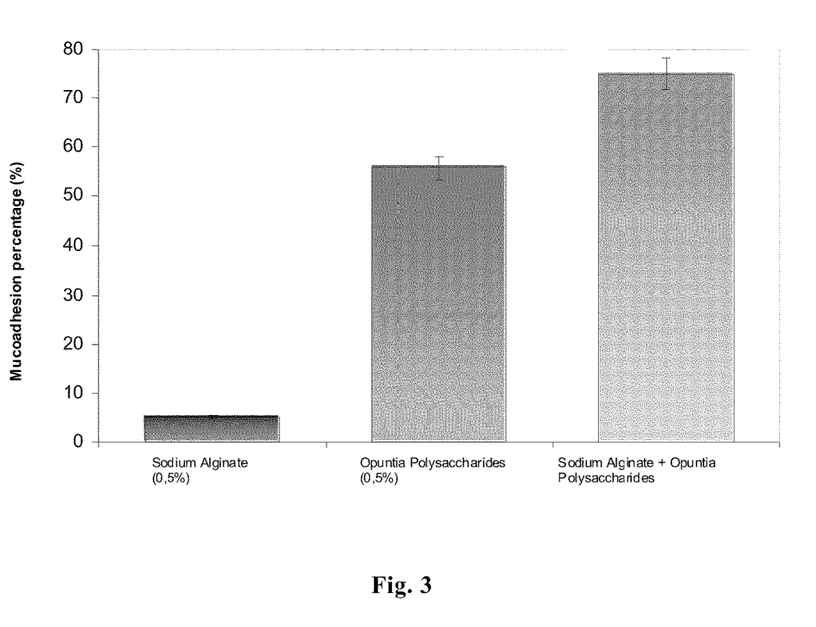
FIG. 3: comparison of the synergistic effect of polysaccharides extracted from *Opuntia Ficus Indica* cladodes with sodium alginate with respect to the individual components in an in vitro model on epithelial buccal mucosa cells.
Figure 4:
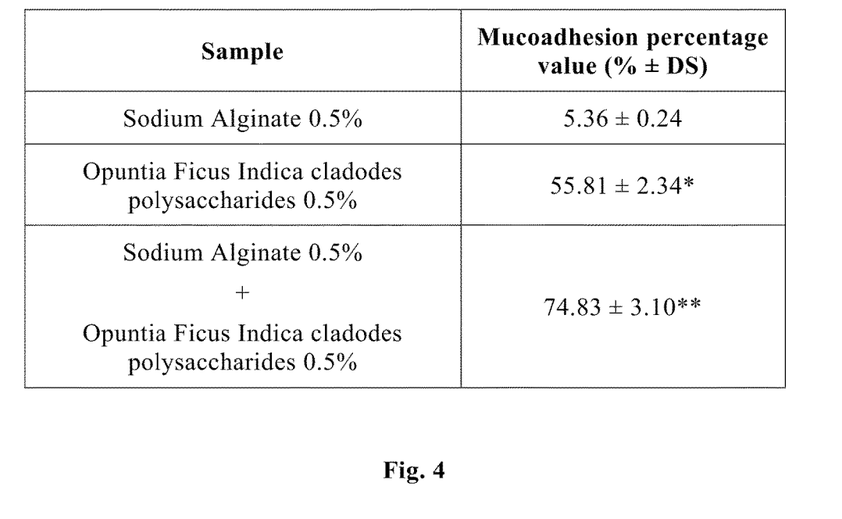
FIG. 4: mucoadhesion (inhibition percentage of lectin binding after treatment) for each tested substances compared in FIG. 3.

As shown in FIGS. 3 and 4, the assay shows a 55.81% *Opuntia Ficus Indica* polysaccharides mucoadhesion to buccal mucosa suspended cells, significantly higher than that observed with sodium alginate (mucoadhesion 5.36%; p<0.05). It was moreover observed that by adding sodium alginate to *Opuntia ficus* Indica cladodes polysaccharides, mucoadhesion reaches 74.83%.

Conclusions

The results obtained with the mucoadhesion in vitro assay showed that *Opuntia Ficus Indica* cladodes polysaccharides exhibit higher mucoadhesion than that observed with sodium alginate. It was moreover unexpectedly found that the combination of these substances determines a synergistic effect that guarantees a strengthened mucoadhesive activity.

In Vivo Evaluation of Antiulcer Activity of a Composition Containing Sodium Alginate/Antacid/*Opuntia Ficus Indica* Cladodes Polysaccharides/*Olea Europeae* Leaves Extract Aim of this study was to assess the antiulcer activity of the combination of sodium alginate/antacid, *Opuntia Ficus Indica* cladodes polysaccharides and *Olea Europeae* leaves extract in an animal model of ethanol- and Indomethacin-induced ulcer (rats).

Materials and Methods

Experimental protocol for the evaluation of 5 test compositions compared to the vehicle: alginate/antacid combination (A), *Opuntia Ficus Indica* cladodes polysaccharides (B), *Olea Europeae* leaves extract (C), alginate\antacid\*Opuntia Ficus Indica* cladodes polysaccharides combination (D), alginate\antacid\*Opuntia Ficus Indica* cladodes polysaccharides\ *Olea Europeae* leaves extract combination (E) and Carbopol 919 0.3% w/v suspension in water as vehicle (F).

Each sample was obtained by water suspension (concentrations reported in Table 7) and administered with an oral pump (1 ml 100 g weight).

TABLE 7 test compositions

| Components | Compositions (% w/v) | | | | | |
|---|---|---|---|---|---|---|
| | A | B | C | D | E | F |
| Sodium Alginate | 5 | — | — | 5 | 5 | — |
| Sodium Bicarbonate | 2.67 | — | — | 2.67 | 2.67 | — |
| Opuntia Ficus Indica cladodes polysaccharides | — | 2 | — | 2 | 2 | — |
| Olea Europeae leaves extract | — | — | 1 | — | 1 | — |
| Carbopol 919 | | | | | | 0.3 |

The experiment was performed on male Wistar (*Rattus norvegicus*) adult rats, weighing from 180 to 200 g. The animals were exposed to natural light (12:12 h light and night cycles) in controlled temperature (24±1° C.) and humidity (60%±4) conditions, and supplied standard food (Morini Mill rat GLP) and water ad libitum for orie week. The animals were then deprived of food 24 hours, and of water 2 hours before the start of the experiment (F. Vitali, *Antiulcer potential of a standardized extract of red orange juice in the rat*, Int J Food Properties, 10, 331-344, 2007).

Experimental Model of Ethanol Induced Ulcer

The animals were randomly divided in 6 groups (1-6) of 6 animals each. Group 1 was used as control and was treated with the vehicle (sample F, Carbopol 919 0.3% w/v and calcium carbonate 1% w/v in distilled water neutralized with NaOH, 1 ml/100 g weight) and, after 1 hour, with the ulcerogenic agent: absolute ethanol 1 ml/rat; groups 2-6 were orally administered samples A (767 mg/kg weight, Group 2), B (200 mg/kg weight—Group 3), C (100 mg/kg weight—Group 4), D (967 mg/kg weight—Group 5) and E (1067 mg/kg weight—Group 6). After 1 hour from administration of samples A-E, the animals of groups 2-6 received 1 ml/animal of absolute ethanol, to induce the ulcer. 1 hour after treatment with ethanol, all animals were anesthetised with diethyl ether and sacrificed. The stomach of each animal was then removed, cutted at the big curve level and gently rinsed with NaCl 0.9% solution, without removing the superficial mucosa.

Experimental Model of Indomethacin-Induced Ulcer

The animals were randomly divided in 6 groups (1-6) of 6 animals each. The animals of Group 1 (control) were orally administered the vehicle (sample F, Carbopol 919 0.3% w/v and calcium carbonate 1% w/v in distilled water neutralized with NaOH, 1 ml/100 g weight) and, after 1 hour, the ulgerogenic agent Indomethacin (suspension in distilled water containing carboxymethylcellulose 1%) at 0.03 g/Kg dose, (1 ml/Kg weight) s.c. Groups 2-6 were treated as described above for ethanol-induced ulcer, with samples A-E and, after 1 hour, with Indomethacin suspension. After 5 hours from the treatment with Indomethacin, the animals were anesthetised with diethyl ether and sacrificed. The stomach of each animal was then removed, and analysed as described in the experiment with ethanol.

Evaluation of the Efficacy of the Tested Compositions

Gastric mucosal surface was visually analysed. The length (mm) of each lesion on the mucosa was determined using an arbitrary scale (Table 8).

In both the experimental models, the ulceration index (U.I) was then calculated for each stomach, adding the scores assigned to the ulcer and the Ulceration Inhibition Percentage (P.I.U.): $[(U.I._{Control} - U.I._{Sample})\backslash U.I._{Control}]$ *100. Data are expressed as arithmetic media±SEM for each group; data significance was analysed by means of Kruskal-Wallis followed by Dunn's test. A p<0.05 value was considered significant.

The ulcer evaluation score for the 2 models is reported in Table 8.

Results

Figure 5:
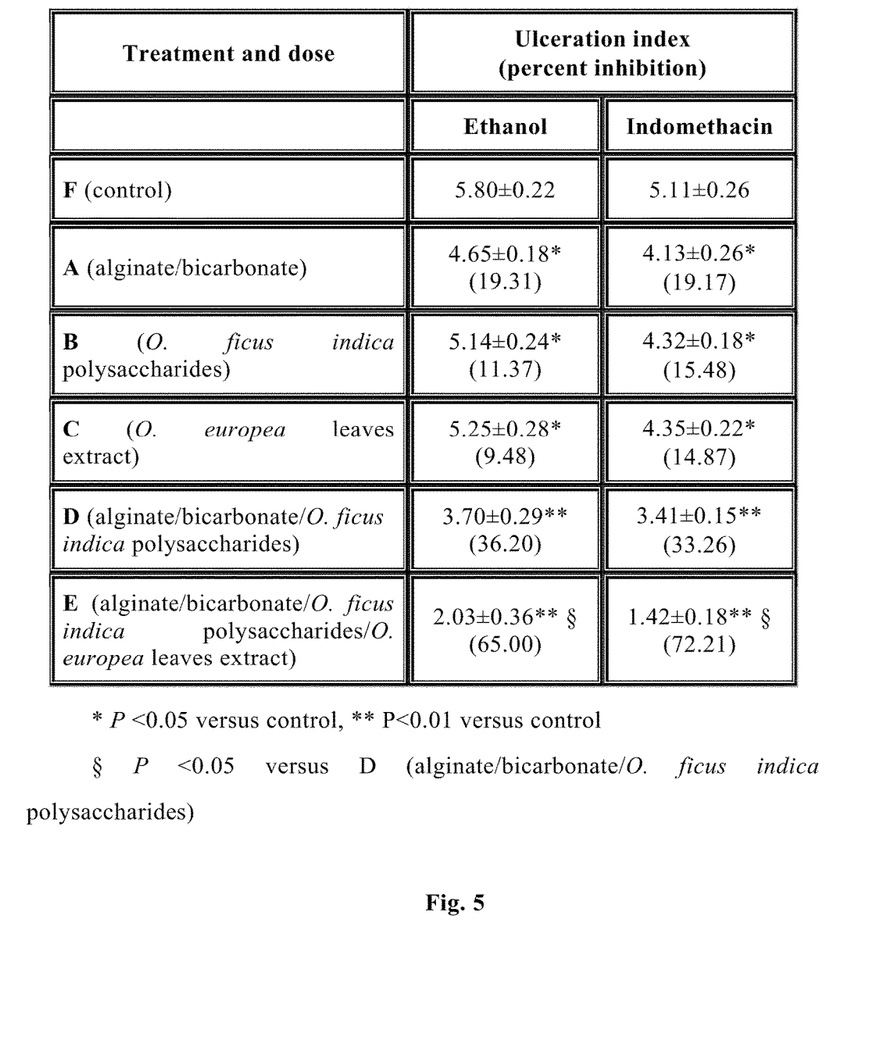
FIG. 5: gastric anti-ulcerogenic effect of different substances or substances combination tested in different experimental models of chemical gastric ulcer in rats. Data are reported as mean±SD of 6 animals; in parenthesis the percent inhibition compared to the control group.

The results of these experiments are illustrated in FIG. 5. In both the experimental models the Ulceration Inhibition Percentage (P.I.U.) obtained with group D (treated with the sodium alginate/antacid/Opuntia Ficus Indica cladodes polysaccharides combination) is higher than that obtained with the individual components of the same combination and higher than the sum of their P.I.U.s, indicating a synergistic effect of the combination of individual substances. Unexpectedly, the addition of *Olea Europeae* leaves extract (group E) increases the P.I.U. by more than the sum of P.I.U.s of *Olea* Europeae leaves extract individual component and sodium alginate/antacid/Opuntia Ficus Indica cladodes polysaccharides combination, revealing their synergistic.

TABLE 8

Ulcer evaluation in the chemically induced ulcer models

| Score | Lesion |
|---|---|
| 0 | No ulcer |
| 0.5 | Hyperemia |
| 1 | Hemorrhagic spots |
| 2 | 1-5 small ulcers |
| 3 | Many small ulcers |
| 4 | 1-5 small ulcers and 1-3 large ulcers |
| 5 | Many small and large ulcers |
| 6 | Stomach full of ulcers along with perforation |

Conclusions

This in vivo test revealed an unexpected synergistic potentiation of the sodium alginate/antacid effect determined by *Opuntia Ficus Indica* cladodes polysaccharides. The synergistic effect is further potentiated by the *Olea Europeae* leaves extract. The ulcer lesions observed in animals receiving conventional treatments (sodium alginate plus sodium bicarbonate) scored very high compared to the animals treated with the combination of the invention, demonstrating a synergistic effect of its individual components.

In Vivo Evaluation of Sodium Alginate/Antacid/Polysaccharides Cladodes *Opuntia Ficus Indica/Olea Europeae* Leaves Extract Combination in Reducing Surgically-Induced Gastroesophageal Reflux (Pyloric Ligation)

Aim of this study was to evaluate the efficacy of the sodium alginate/antacid/polysaccharides cladodes *Opuntia Ficus Indica* combination added with *Olea Europeae* leaves extract in reducing the gastroesophageal reflux surgically induced by pyloric ligation in rats.

The reduction of gastroesophageal reflux was measured from the esophageal ulcers in animals treated with the active combinations after surgical induction.

Adult Wistar male rats (*Rattus norvegicus*) weighing 180-200 grams were randomly divided in 6 groups (1-6), each of 6 animals. According to the experimental protocol described by Min (Min et al.: *The effects of apigenin-7-O-β-D-glucurono-pyranoside on reflux oesophagitis and gastritis in rats*, Autonomic & autacoid Pharmacology 2005 July; 25(3):85-91; Hayakawa T. et al.: *Roles of cyclooxygenase 2 and microsomal prostaglandin E synthase 1 in rat acid reflux oesophagitis*, Gut 2006, 55: 450-456), the animals were anesthetised with pentobarbital and acid reflux esophagitis was induced by ligating the transitional region between the forestomach and the glandular portion and wrapping the duodenum near the pylorus. Group 1 (not treated) was the positive control. Groups 2-6 were intraduodenally treated with compositions A-E immediately after the ligation of pylorus and limiting ridge, using the same dosages as in the chemically-induced ulcer models described above. Afterwards, a longitudinal cardiomyotomy of about 1 cm across the gastro-oesophageal junction was performed to enhance reflux from the stomach into the esophageal body. After 6 h, the animals were sacrificed under diethyl ether anaesthesia and the esophagus was harvested and the lesions total area scored as reported in Tab. 9.

The final ulceration index (U.I.) and the P.I.U. for each group were calculated as described above.

TABLE 9

Esophageal mucosa lesions evaluation

| Score | Total area (mm$^2$) |
|---|---|
| 0 | No visibile lesions |
| 1 | Rare lesions |
| 2 | Total lesions area ≤30 mm$^2$ |
| 3 | Total lesions area ≥30 mm$^2$ |
| 4 | Perforation |

Results

Figure 6:
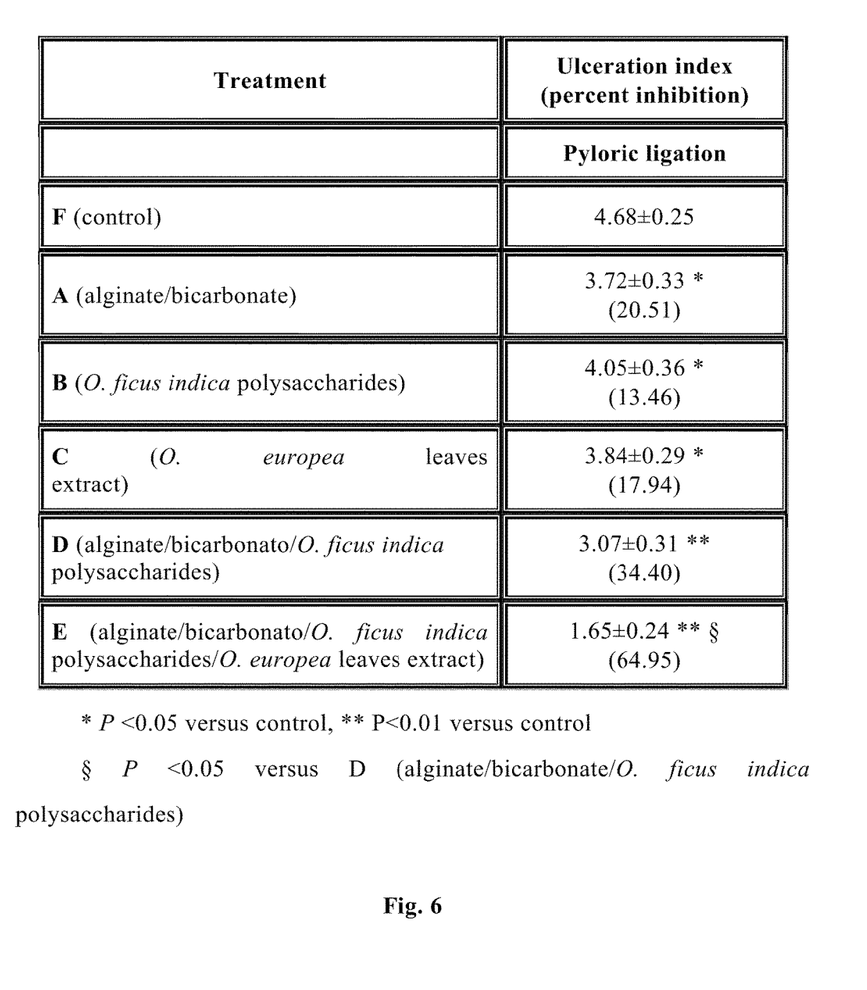
FIG. 6: esophageal anti-ulcerogenic effect of different substances or substances combination tested in a model of gastroesophageal reflux surgically induced. Data are reported as mean±SD of 6 animals; in parenthesis the percent inhibition compared to the control group.

The results of this experiment are reported in FIG. 6. This experimental model confirmed the higher Ulceration Inhibition Percentage (P.I.U.) obtained with group D (treated with the sodium alginate/antacid/Opuntia Ficus Indica cladodes polysaccharides) than that observed in the experimental groups treated with the individual components and even higher than the sum of their P.I.U.s, revealing a marked synergistic effect of the sodium alginate/antacid/*Opuntia Ficus Indica* cladodes polysaccharides combination in reducing the gastroesophageal reflux. The further addition of *Olea Europeae* leaves extract to this combination (group E) increased the P.I.U. to a level higher than the sum of *Olea Europeae* leaves extract individual component and combination D P.I.U.s., confirming the results obtained in the chemically-induced gastric ulcer models.

CONCLUSIONS

This in vivo test shows that *Opuntia Ficus Indica* cladodes extract has a potentiating effect in reducing the gastroesophageal reflux. This effect is further increased by the addition of *Olea Europeae* leaves extract.

The invention claimed is:

1. An oral solid composition for treating diseases of the upper gastrointestinal tract, comprising a synergistic combination of:
   1-20 g Opuntia ficus indica cladodes polysaccharides;
   5-20 g Olea europeae leaf extract;
   5-10 g sodium bicarbonate; and
   10-20 g sodium alginate,
   wherein said diseases are selected from the group consisting of gastroesophageal reflux, GERD, dyspepsia, gastrointestinal disturbs, pharyngitis, Barrett's esophagus, esophageal adenocarcinoma, and GERD-related pulmonary symptoms.

2. The composition according to claim 1, wherein said cladodes polysaccharides are provided as mucilages, cladode juice, or a filtered cladode juice aqueous solution that is optionally concentrated and dried.

3. The composition according to claim 1, which is in the form of a pharmaceutical or nutraceutical preparation, health food or medical device composition.

4. The composition according to claim 3, which is in the form of a tablet, capsule, or powder.

\* \* \* \* \*